(12) United States Patent
Ressler

(10) Patent No.: US 7,217,936 B2
(45) Date of Patent: May 15, 2007

(54) SYSTEM AND METHOD FOR PRODUCT STERILIZATION USING UV LIGHT SOURCE

(76) Inventor: Barry Ressler, 137 Lake Pl. South, Danbury, CT (US) 06810

( * ) Notice: Subject to any disclaimer, the term of this patent is extended or adjusted under 35 U.S.C. 154(b) by 0 days.

(21) Appl. No.: 11/056,698

(22) Filed: Feb. 11, 2005

(65) Prior Publication Data

US 2005/0173652 A1    Aug. 11, 2005

Related U.S. Application Data

(60) Provisional application No. 60/543,710, filed on Feb. 11, 2004.

(51) Int. Cl.
*A61L 2/10* (2006.01)
*A61L 2/26* (2006.01)
(52) U.S. Cl. .............................. 250/455.11; 250/504 R
(58) Field of Classification Search ........... 250/455.11, 250/504 R
See application file for complete search history.

(56) References Cited

U.S. PATENT DOCUMENTS

| | | | | |
|---|---|---|---|---|
| 5,468,803 A | * | 11/1995 | Takahashi et al. | .......... 524/553 |
| 6,465,799 B1 | * | 10/2002 | Kimble et al. | .......... 250/504 R |
| 6,586,749 B2 | * | 7/2003 | Cimino et al. | ......... 250/455.11 |
| 2003/0062483 A1 | * | 4/2003 | Cimino et al. | .......... 250/432 R |

* cited by examiner

*Primary Examiner*—Nikita Wells
*Assistant Examiner*—Johnnie L Smith, II
(74) *Attorney, Agent, or Firm*—Robert L. Epstein; Epstein Drangel Bazerman & James, LLP

(57) ABSTRACT

System and method for sterilization, using UV light source(s), of products, e.g., polymer-based products, whether positioned within or external to their packaging, using monochromatic, continuous wave, high-intensity, incoherent light in single and/or multiple light source configurations. The treatment system(s) and method(s) may be used for sterilization of alternative products, including, for example, food products such as meat and poultry, enteral and/or parenteral solutions and systems, and the like.

7 Claims, 2 Drawing Sheets

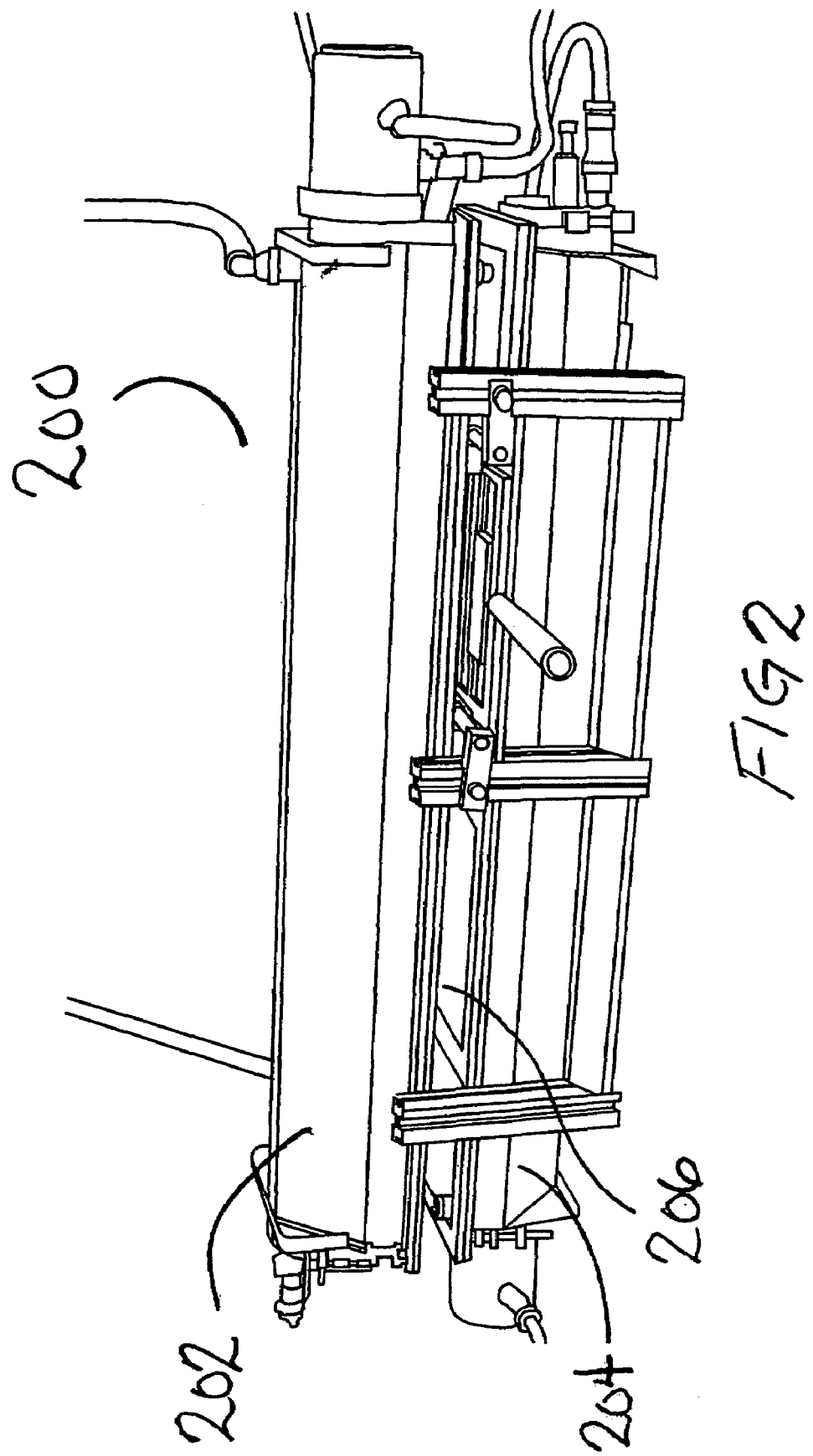

SYSTEM AND METHOD FOR PRODUCT STERILIZATION USING UV LIGHT SOURCE

This application claims the benefit of U.S. Provisional Application No. 60/543,710 filed Feb. 11, 2004.

BACKGROUND

1. Technical Field

The present disclosure is directed to system(s) and method(s) for sterilization of products and/or systems using UV light source(s). More particularly, the present disclosure is directed to system(s) and method(s) for sterilization of polymer-based products, whether positioned within or external to their packaging, using monochromatic, continuous wave, high-intensity, incoherent light in single and/or multiple light source configurations. The disclosed treatment system(s) and method(s) advantageously preserve physical and performance properties of the product/system while achieving a desired level of sterilization. The disclosed treatment system(s) and method(s) may be used for sterilization of alternative products, including, for example, food products such as meat and poultry, enteral and/or parenteral solutions and systems, and the like.

2. Background Art

Sterilization is generally defined as the complete destruction of all organisms, including a large number of highly resistant bacterial endospores. A host of sterilization techniques have been developed to address specific sterilization needs. Typical sterilization techniques include the use of moist heat from a steam autoclave, ethylene oxide gas sterilizing techniques, dry heat techniques, and newer chemical sterilizers.

Steam sterilization is widely used and is generally viewed as relatively cost-effective sterilization technique. The use of steam sterilization techniques employing an autoclave is recognized as an efficient, simple, and relatively cost-effective approach for destroying all relevant organisms. However, certain components (e.g., medical device/instrumentation components and accessories) cannot endure the extremes of heat and pressure. For example, steam and pressure are known to damage rubber, Lexan® plastic components, and other synthetic materials, and the use of a steam autoclave for any anesthesia equipment is generally not recommended, unless the treatment method is specifically recommended by the manufacturer.

Ethylene oxide is acceptable for many materials used in manufacturing medical devices and the like, including the reusable components of anesthesia machines, ventilators, and monitors. However, it is generally inappropriate to place these entire systems in an ethylene oxide chamber. In addition, polystyrene component parts cannot be exposed to ethylene oxide gas. Ethylene oxide sterilization employs a powerful poisonous fumigant gas, and therefore mandates an appropriate means of aeration to remove all traces of residual gas. Workers exposed to ethylene oxide are required to comply with all procedures specified by OSHA and the EPA. Alternative chemical treatment techniques include the use of hydrogen peroxide and peroxyacetic acid with buffers and low heat.

More recently, a sterilization technique was disclosed in U.S. Pat. No. 5,786,598 to Clark et al., entitled "Sterilization of Packages and Their Contents Using High-Intensity, Short-Duration Pulses of Incoherent, Polychromatic Light in a Broad Spectrum." As noted in the title, the Clark '598 patent involves the use of high-intensity, short-duration pulses of incoherent, polychromatic light in a broad spectrum to sterilize product containers and deactivate microorganisms therein. The Clark '598 proposes "the deactivation of microorganisms within parenteral and/or enteral solutions and packages or within contact lens solutions and packages and/or ophthalmic solutions and packages." [See col. 1, lines 11–20.] The use of short-duration pulses of incoherent, polychromatic light in a broad spectrum, as disclosed in the Clark '598 patent, is believed to be ineffective and/or unacceptable for at least some aspects of the proposed applications.

Despite efforts to date, a need remains for system(s) and/or method(s) for use in sterilizing polymer-based product(s), whether positioned within or external to their packaging, wherein such treatment regimen achieves a desired sterilization level without negatively affecting the physical properties and/or the efficacy of the underlying polymer-based product(s). A need also exists for system(s) and/or method(s) for use in sterilizing alternative products (e.g., food products such as meat and poultry, enteral and/or parenteral solutions and systems, and the like), whether positioned within or external to their packaging, wherein such treatment regimen achieves a desired sterilization level without negatively affecting the physical properties and/or the efficacy of the underlying product(s).

These and other objectives are satisfied according to the present disclosure wherein sterilization is achieved using monochromatic, continuous wave, high-intensity, incoherent light in single and/or multiple light source configurations. The disclosed treatment system(s) and method(s) advantageously achieve a desired sterilization level without negatively affecting the physical properties and/or the efficacy of the underlying product(s). These and other features/functionalities will be apparent to persons skilled in the art from the detailed description which follows.

SUMMARY OF THE DISCLOSURE

An advantageous approach for the sterilization of products, including heat sensitive materials, whether within or external to their packaging and/or packaging containers, is disclosed herein. The disclosed sterilization system(s) and method(s) are effective in inactivating viral and bacterial microorganisms without physical or performance damage to the treated product or its packaging. A single or multiple array of light sources delivers monochromatic germicidal, ambient temperature light at radiance levels of at least 200 mw/cm$^2$ to 600 mw/cm$^2$ to deactivate multiple organisms. According to exemplary embodiments of the present disclosure, products are sterilized to Sterilization Assurance Levels (SALs) of at least $10^{-5}$ cfu/ml at discrete wavelengths of 193; 222; 248; 282; 308 and 354 nm (+/−5 nm).

The disclosed sterilization treatment regimen may be undertaken in a batch, semi-batch or continuous mode. In an exemplary embodiment of the present disclosure, target product(s) and/or container-packaged product(s) are treated continuously by positioning the product(s)/container(s) on a moving element (e.g., a belt) that is moved above, below or between one or more light sources. The rate at which the product(s)/container(s) are moved past the light source(s) may be adjusted so as to achieve the desired energy treatment level. In batch/semi-batch embodiments, the treatment time may be varied to achieve the desired energy treatment level. As noted below, additional processing parameters affect the sterilization procedure, and may be adjusted/selected (either alone or in combination with the rate/residence time) to achieve the desired sterilization result(s).

Thus, the intensity of the monochromatic light source(s) that are employed according to the sterilization system(s) and/or method(s) of the present disclosure may be adjusted to achieve the desired sterilization results. For example, in processing systems wherein multiple light sources are employed, the individual light sources may be operated at different intensities to achieve the desired sterilization results. Light source intensity is generally selected based on the treatment algorithm for a single microorganism or suite (panel) of organisms/microorganisms. In typical treatment regimens, the panel of organisms includes, but is not limited to, *Bacillus pumilus* (spore former), *Candida albican* (yeast), lipid and non-lipid virus, *Clostridium sporogenes* (anaerobic spore former), *Staphylococcus aureus* (vegetative Gram positive), *Pseudomonas aeruginosa* (vegetative Gram negative), *Aspergillus niger* (filamentous fungi), *Mycobacterium terrae*, Porcine Parvo Virus (PPV and B19), Lysteria, and Salmonela. The sterilization treatment regimen disclosed herein is effective in treating products/packaging of varying geometries. Thus, for example, the product and/or product package may be planar, convex, concave or an alternative geometry, e.g., a geometric combination of the foregoing geometries. The light sources may be modified to achieve desired results. Thus, for example, partially coated optical surfaces may be employed, such coated surfaces being advantageously tuned to a desired monochromatic wavelength. The use of partially coated optical surfaces may be effective in generating light that satisfies spectral intensity requirements in excess of 500 mw/cm$^2$.

Additional features and functionalities associated with the disclosed sterilization system(s) and method(s) will be apparent from the detailed description which follows, particularly when viewed together with the figures appended hereto.

BRIEF DESCRIPTION OF THE FIGURES

To assist those of ordinary skill in the art to which the present disclosure appertains in making and using the disclosed sterilization system(s) and method(s), reference is made to the appended figures, wherein:

FIG. 2 is a photograph (side view) of an alternative exemplary sterilization system/assembly for delivering monochromatic, continuous wave, high-intensity, incoherent light to products, e.g., polymer-based products, using dual light sources (top and bottom) according to the present disclosure.

DETAILED DESCRIPTION OF EXEMPLARY EMBODIMENT(S)

Figure 1A:
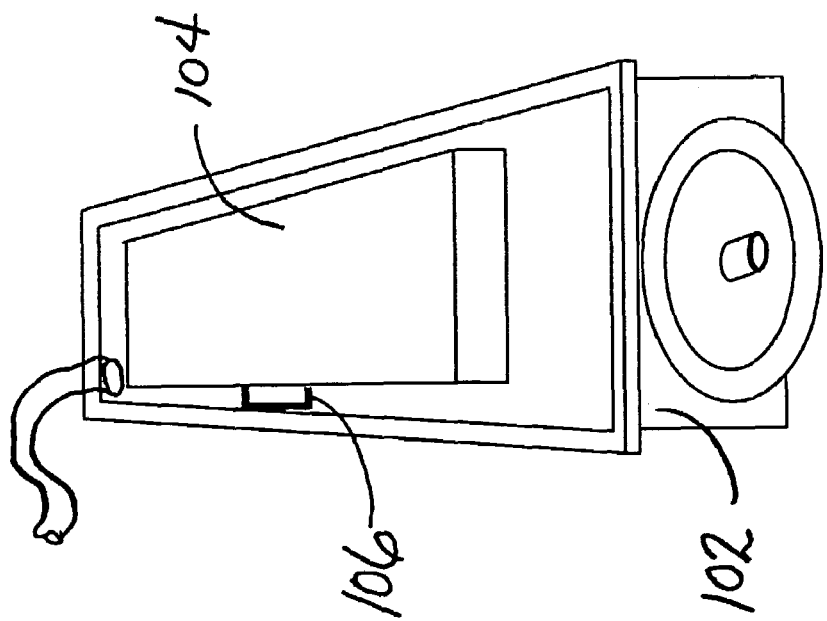
FIG. 1A is a photograph (side view) of the exemplary sterilization system/assembly of FIG. 1, with the cover structure positioned in a closed position.

According to the present disclosure, systems and methods for sterilization of products, including heat sensitive materials, whether within or external to their packaging and/or packaging containers, are provided. These systems/methods are effective in inactivating viral and bacterial microorganisms without physical or performance damage to the treated product or its packaging. A single or multiple array of light sources delivers monochromatic germicidal, ambient temperature light at irradiance levels of at least 200 mw/cm$^2$ to 600 mw/cm$^2$ to deactivate multiple organisms. According to exemplary embodiments of the present disclosure, products (e.g., packaged contact lenses) are sterilized to Sterilization Assurance Levels (SALs) of at least $10^{-5}$ cfu/ml (colony forming units/milliliter) at discrete wavelengths of 193; 222; 248; 282; 308 and 354 nm (+/−5 nm). Currently preferred wavelengths for use in sterilizing treatments of polymeric contact lens products (whether packaged or non-packaged) are 282 and 308 nm.

The disclosed sterilization treatment regimen may be undertaken in a batch, semi-batch or continuous mode. The application of monochromatic UV light using the disclosed light source(s) to inactivate viral and bacterial microorganisms in sterilizing contact lenses is a particularly attractive alternative to currently practiced sterilization methods, such as steam sterilization, because the disclosed UV radiation treatment is readily incorporated into an in-line (i.e., continuous or substantially continuous) process, in which the sterilization may be accomplished in a matter of seconds or less. In addition, the disclosed monochromatic UV light is effective for sterilization of heat sensitive materials without negatively affecting physical properties and/or performance attributes thereof. Additional performance features/functionalities associated with such polymer-based products (e.g., contact lenses) that were not feasible with conventional steam sterilization (e.g., because steam sterilization damaged or destroyed such features/functionalities) are potentially feasible using the disclosed monochromatic UV sterilization technique.

In an exemplary embodiment of the present disclosure, target product(s) and/or container-packaged product(s) are treated continuously by positioning the product(s)/container(s) on a moving element (e.g., a belt) that is moved above, below or between one or more light sources. For example, with reference to FIG. 2, top and bottom light sources define an intermediate region in which products (e.g., packaged contact lenses) may be transported for sterilization treatment. A variety of structures and mechanisms may be used to transport products through the intermediate region while permitting UV radiation to reach the products for sterilization purposes, e.g., conveyor belts and/or tracks of various designs and constructions. The selection and implementation of appropriate conveyor/transport systems is well within the skill of persons skilled in the art. It is further expressly noted that transport systems may be incorporated in single light source implementations of the disclosed sterilization systems, e.g., of the type depicted in FIG. 1 hereto.

The rate at which the product(s)/container(s) are moved past the light source(s) in continuous or semi-continuous embodiments of the present disclosure may be adjusted so as to achieve the desired energy treatment level. Similarly, in batch/semi-batch embodiments, the treatment time may be varied to achieve the desired energy treatment level. As noted below, additional processing parameters affect the sterilization procedure, and may be adjusted/selected (either alone or in combination with the rate/residence time and/or other processing parameters) to achieve the desired energy delivery and resultant sterilization effect(s).

Thus, the intensity of the monochromatic light source(s) that are employed according to the sterilization system(s) and/or method(s) of the present disclosure may be adjusted to achieve the desired sterilization results. For example, in processing systems wherein multiple light sources are employed, the individual light sources may be operated at different intensities and/or for different periods of time to achieve the desired sterilization results. A control system may be advantageously associated with the light source(s) to control operating parameters thereof. A typical control system includes a processor that is programmed to operate the light sources at desired intensity levels and for desired period(s) of time. In the case of continuous treatment regimens, the control system may also advantageously control the rate at which products pass through the treatment region, e.g., based on the speed of the conveyor/transport system. A manual over-ride is typically provided, so as to permit an operator to adjust/modify treatment parameters on an as-needed basis.

Treatment parameters, e.g., light source intensity, are generally selected based on the treatment algorithm for a single microorganism or suite (panel) of organisms/microorganisms. In typical treatment regimens, the panel of organisms includes, but is not limited to, *Bacillus pumilus* (spore former), *Candida albican* (yeast), lipid and non-lipid virus, *Clostridium sporogenes* (anaerobic spore former), *Staphylococcus aureus* (vegetative Gram positive), *Pseudomonas aeruginosa* (vegetative Gram negative), *Aspergillus niger* (filamentous fungi), *Mycobacterium terrae*, Porcine Parvo Virus (PPV and B19), Lysteria, and Salmonela. Additional and/or alternative organisms may be utilized, in whole or in part, in developing and implementing an appropriate treatment regimen, as will be readily apparent to persons skilled in the art. Sterilization treatment regimens utilizing monochromatic germicidal, ambient temperature light, as disclosed herein, are effective in treating products/packaging of varying geometries. Thus, for example, the product and/or product package may be planar, convex, concave or an alternative geometry, e.g., a geometric combination of the foregoing geometries. The light sources may be modified to achieve desired sterilization results. Thus, for example, partially coated optical surfaces may be employed, such coated surfaces being advantageously tuned to a desired monochromatic wavelength. The use of partially coated optical surfaces may be effective in generating light that satisfies spectral intensity requirements in excess of 500 mw/cm$^2$.

Light source systems according to the present disclosure emit light over a large active area and are advantageously configured to operate at ambient temperatures. The substantially monochromatic output of these sources can be tuned to produce high spectral irradiance (watts/nm) within peaks of the process action spectra to maximize the germicidal effectiveness (or other desired process/application) as a function of the required biological objective. The range of available geometries (including coaxial sources radiating either inwardly or outwardly, and planar sources emitting from one or both sides) and the capability to independently adjust irradiance and total power provide significant flexibility in system design and allow for more efficient light delivery systems.

Figure 1:
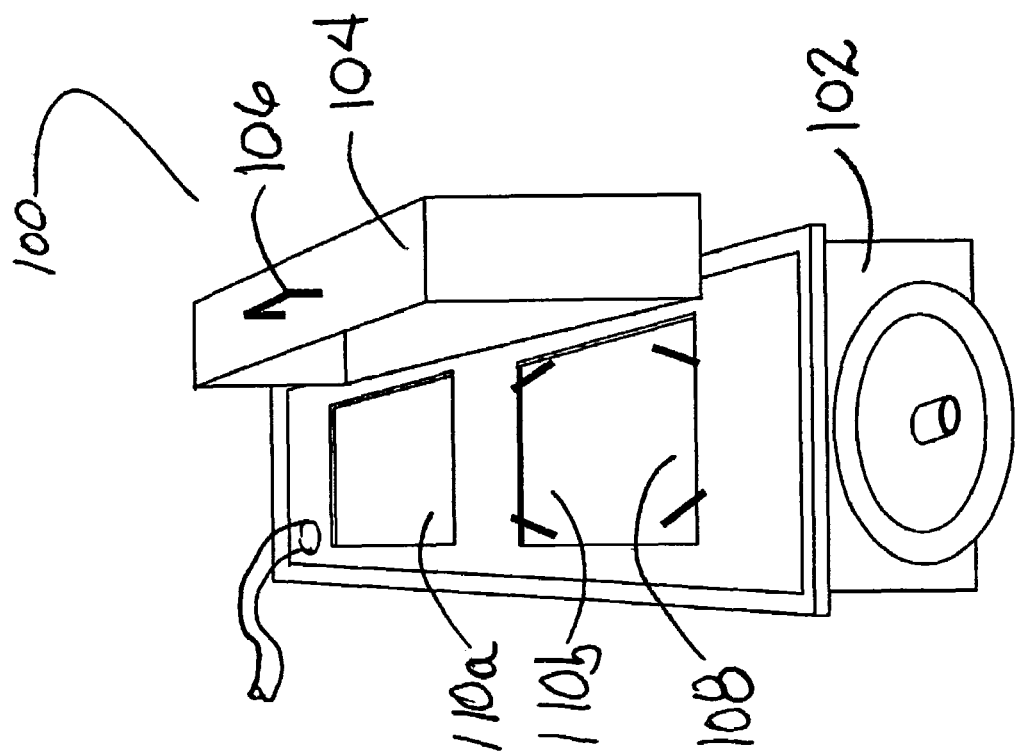
FIG. 1 is a photograph (top view) of an exemplary sterilization system/assembly for delivering monochromatic, continuous wave, high-intensity, incoherent light to products, e.g., polymer-based products, using a single light source according to the present disclosure.

With particular reference to FIGS. 1 and 1A, exemplary treatment system 100 includes a base structure 102 and a cover structure 104. Cover structure 104 is hingedly mounted with respect to base structure 102 and includes a handle 106 to facilitate repositioning thereof (i.e., opening/closing). FIG. 1 shows cover structure 104 in an "open" position, and FIG. 1A shows cover structure 104 in a "closed" position. Cover structure 104 is typically fabricated from a material that is effective in filtering/shielding the light rays produced by the light source so as to protect operators and others in the vicinity of treatment system 100. Thus, the size and geometry of cover structure 104 is typically selected so as to permit positioning of product(s) in an appropriate treatment position relative to the light source, while ensuring that the emitted light rays are filtered/shielded thereby.

Treatment system 100 includes a light source 108 positioned within base structure 102 that is designed to generate and emit monochromatic germicidal, ambient temperature light through treatment windows 110a, 110b. Light source 108 is an excimer light source that generally produces 90% of its output within a 10 nm band that can be discretely adjusted across the VUV, UV-A, UV-B and UV-C by changing the rare and/or halogen gases used. Efficiencies vary with gas mix and geometry from 10% to >30% with demonstrated input powers from <1 watt to >10 kW. The overall design and operation of exemplary light sources for use in the disclosed system are disclosed, described and depicted in commonly assigned patent applications, Ser. No. 09/805,610 (filed Mar. 13, 2001; published as U.S. Pat. Ser. No. 2002-0177118 A1) and Ser. No. 10/661,262 (filed Sep. 12, 2003) (the "Prior Applications"), the entire contents of which are hereby incorporated by reference in their entireties. For example, the Prior Applications disclose and describe exemplary flow patterns/arrangements for the introduction and withdrawal of cooling fluids (e.g., see tubing/hoses in FIGS. 1 and 1A), exemplary treatment window designs and the like, each of which is visually apparent in FIG. 1 and/or FIG. 1A.

According to exemplary embodiments of the disclosed systems, an appropriate fluid is used to maintain the light source(s) at a desired temperature and/or within a desired temperature range. Water is a preferred heat exchange medium for dissipating/absorbing heat generated through operation of the light source(s). However, alternative cooling fluids may be employed, as will be apparent to persons skilled in the art. In selecting an appropriate cooling fluid, it is desirable to select a fluid that, in use, is substantially transparent to the germicidal radiation to be passed therethrough. Of note, it is also desirable to select a fluid that is not susceptible to bubble generation and/or bubble propagation, because the presence/formation of bubbles can undesirably scatter germicidal radiation and negatively effect the sterilization efficiency and/or effectiveness of the disclosed system. Thus, precautions may be advantageously taken to minimize and/or prevent bubble formation/propagation in cooling fluid use, e.g., through the use of appropriate additives or the like.

Thus, in use, products for sterilization, e.g., contact lens products, medical products and/or components, food products and the like (whether packaged or non-packaged) are positioned above a window 110a, 110b, the cover structure 106 is "closed" so as to shield the treatment region, and the light source 108 is energized to deliver monochromatic germicidal, ambient temperature light thereto. The light source is advantageously maintained at a substantially controlled temperature through heat transfer/heat exchange modalities, as described in the Prior Applications. As noted above, the Prior Applications are incorporated herein by reference in their entireties.

With reference to FIG. 2, a further exemplary treatment system 200 is depicted. System 200 includes a first (upper) light source housing 202 and a second (lower) light source housing 204. Light sources (not visible) are positioned within housings 202, 204 and are advantageously maintained at a substantially constant temperature utilizing heat transfer/heat exchange modalities, as described in the Prior Applications. A treatment region 206 is defined between housings 202, 204. Treatment windows (not visible) are defined in the first and second housings 202, 204, such that monochromatic germicidal light from the respective light sources may reach products within treatment region 206.

A conveyor/transport system (not visible) is advantageously provided for transporting products through treatment region 206, i.e., between housings 202, 204. According to exemplary embodiments of the present disclosure, the conveyor may advance the products through treatment region 206 in a fixed orientation relative to the light source(s). Alternatively, in may be desirable to include structure(s) and/or mechanism(s) that are effective to cause repositioning of the products relative to the light source(s) as they pass through the treatment region. For example, in the case of thick and/or irregularly shaped products, it may be desirable to effect rotation of the products at one or more points within the treatment region. Effective structure(s) and/or mechanism(s) for effecting reorientation of the products within the treatment region may be associated with the conveyor, with the upper and/or lower housings, or a combination thereof. The repositioning of the products may be effected in a substantially random fashion, e.g., by providing diverter walls or the like, or may be effected in a controlled fashion, e.g., through controlled robotics or the like. In any case, the inclusion of a repositioning mechanism may be desirable to provide efficient and reliable sterilization treatments to products of various sizes and geometries.

The distance between upper housing 202 and lower housing 204 is generally selected to permit passage of desired products therebetween with minimal clearance. According to exemplary embodiments of the present disclosure, the spacing between housings 202, 204 may be adjusted, e.g., by repositioning at least one of housings 202, 204 relative to the other housing. Thus, for example, upper housing 204 may be supported by a frame structure that permits/facilitates vertical repositioning thereof relative to lower housing 202 (e.g., through manual or powered repositioning of upper housing 204). As noted previously, the light source within upper housing 204 may be designed/configured to deliver monochromatic light having different characteristics relative to the light source within lower housing 202. Thus, the dual light source arrangement of FIG. 2 further enhances the flexibility/versatility of the disclosed sterilization regimens according to the present disclosure.

According to the present disclosure, a sterilization assurance level (SAL) of $10^{-6}$ may be achieved for inoculated product and packaging that include a panel that may include (but are not limited to) *Bacillus pumilus* (spore former), *Candida albican* (yeast), Lipid and non-lipid virus, *Clostridium sporogenes* (anaerobic spore former), *Staphylococcus aureus* (vegetative Gram positive), *Pseudomonas aeruginosa* (vegetative Gram negative), *Aspergillus niger* (filamentous fungi), *Mycobacterium terrae*, Porcine Parvo Virus (PPV and B19), Lysteria, Salmonela. In achieving the foregoing SAL, the overall performance properties of the sterilized products (whether packaged or non-packaged), e.g., contact lenses or the like, are not materially affected.

In operating the disclosed sterilization treatment systems, numerous processing variables and/or product properties may influence the effectiveness of the sterilization treatment and/or the associated product survivability criteria (i.e., post-sterilization product performance and/or efficacy). For example, exemplary processing variables and product properties that may require consideration in developing appropriate/optimal processing parameters for contact lenses include:

Power delivery to light sources (Power is directly related to the UV radiation dose delivered to products)

Treatment time (Treatment time is directly related to the UV radiation dose delivered to products)

Base Curve of contact lenses to be treated (Base curve radius may influence the desired/optimal UV radiation dose)

Diameter of contact lenses to be treated (Diameter may influence the desired/optimal UV radiation dose)

Oxygen Permeability of contact lenses (Oxygen permeability may influence the desired/optimal UV radiation dose)

Equilibrium Water Content of contact lenses (Equilibrium water content may influence the desired/optimal UV radiation dose)

Modulus of contact lenses (Modulus may influence the desired/optimal UV radiation dose)

Elongation at break of contact lenses (Elongation at break may influence the desired/optimal UV radiation dose)

Tensile Strength of contact lenses (Tensile strength may influence the desired/optimal UV radiation dose)

Toughness modulus of contact lenses (Toughness modulus may influence the desired/optimal UV radiation dose)

Although the present disclosure has been described with reference to exemplary embodiments thereof, it is to be understood that the disclosure is not limited thereto. Rather, the systems and methods disclosed herein encompass modifications, enhancements and/or variations that will be readily apparent to persons skilled in the art, based on a review of the present disclosure, including specifically the Prior Applications incorporated herein by reference in their entireties.

The invention claimed is:

1. Apparatus for sterilization of ophthalmic products such as contact lenses comprising non-attenuated, monochromatic, continuous wave, high intensity, incoherent light source means including cooling fluid to maintain same within a desired temperature range, a housing enclosing no more than one light source means therein, without additional means for cooling said enclosed light source means, said housing having a wall with substantially planar, substantially transparent section defining a treatment area within which the product to be sterilized is situated, and means for covering said treatment area when said light source means is energized.

2. The apparatus of claim 1 wherein said light source means comprises a bounded volume of photon-producing gas.

3. The apparatus of claim 1 wherein said light source generates light with wavelengths of 193, 222, 248, 282, 308 and 354 nm, in a sterilization dosage.

4. Apparatus for sterilization of ophthalmic products such as contact lenses comprising first and second non-attenuated, mono-chromatic, continuous wave, high intensity, incoherent light source means, each including cooling fluid to maintain same within a desired temperature range, first and second housings each respectively enclosing no more than one light source means therein, without additional means for cooling said enclosed light source, each of said housings having a wall with a substantially planar, substantially transparent section, said housings being situated in spaced relation, with said planar transparent sections of each facing each other, so as to define a treatment area therebetween and means for retaining the product to be sterilized in said treatment area.

5. The apparatus of claim 4 wherein said product retaining means comprises means for moving said product through said treatment area.

6. The apparatus of claim 4 wherein each of said light source means comprises a bounded volume of photon-producing gas.

7. The apparatus of claim 4 wherein each of said light source means generates light with wavelengths of 193, 222, 248, 282, 308 and 354 nm, in a sterilization dosage.

* * * * *